United States Patent [19]

Bhatia

[11] Patent Number: 5,136,057

[45] Date of Patent: Aug. 4, 1992

[54] HIGH YIELD RECYCLE PROCESS FOR LACTIDE

[75] Inventor: Kamlesh K. Bhatia, Newark, Del.

[73] Assignee: E. I. Du Pont de Nemours and Company, Wilmington, Del.

[21] Appl. No.: 780,821

[22] Filed: Oct. 22, 1991

Related U.S. Application Data

[63] Continuation of Ser. No. 552,217, Jul. 13, 1990, abandoned.

[51] Int. Cl.$^5$ ............... C07D 319/12; C07C 51/48; C07C 59/08
[52] U.S. Cl. ................... 549/274; 562/580; 562/589
[58] Field of Search ............... 549/274; 562/580, 589

[56] References Cited

U.S. PATENT DOCUMENTS

| | | | |
|---|---|---|---|
| 1,095,205 | 5/1914 | Grüter et al. | 549/274 |
| 2,668,162 | 2/1954 | Lowe | 549/274 |
| 2,703,316 | 3/1955 | Schneider | 264/78.3 |
| 3,878,284 | 4/1975 | Schmitt et al. | 264/184 |
| 4,033,938 | 7/1977 | Augurt et al. | 260/78.3 |
| 4,727,163 | 2/1988 | Bellis | 549/274 |
| 4,797,468 | 1/1989 | De Vries | 549/274 |
| 4,800,219 | 1/1989 | Murdoch et al. | 525/413 |
| 4,835,293 | 5/1989 | Bhatia | 549/274 |
| 4,895,681 | 1/1990 | Herrmann et al. | 260/410 |
| 4,966,982 | 10/1990 | Ono et al. | 549/274 |
| 4,983,745 | 1/1991 | Muller et al. | 549/274 |
| 4,990,222 | 2/1991 | Aigner et al. | 203/91 |

FOREIGN PATENT DOCUMENTS

| | | |
|---|---|---|
| 3632103 | 3/1988 | Fed. Rep. of Germany . |
| 3708915 | 9/1988 | Fed. Rep. of Germany . |
| 9001521 | 2/1990 | World Int. Prop. O. . |

*Primary Examiner*—Richard L. Raymond
*Assistant Examiner*—Mark W. Russell
*Attorney, Agent, or Firm*—Charles E. Krukiel

[57] ABSTRACT

Processes are described for recovering lactic acid from impure lactide and the residue produced in the depolymerization of polylactic acid to lactide. Lactic acid is recovered from the impure lactide by a dual solvent extraction process and, from the polylactic acid residue by hydrolysis. The lactic acid recovered from the impure lactide and the depolymerization residue is recycled to provide for a high yield lactide process.

15 Claims, 1 Drawing Sheet

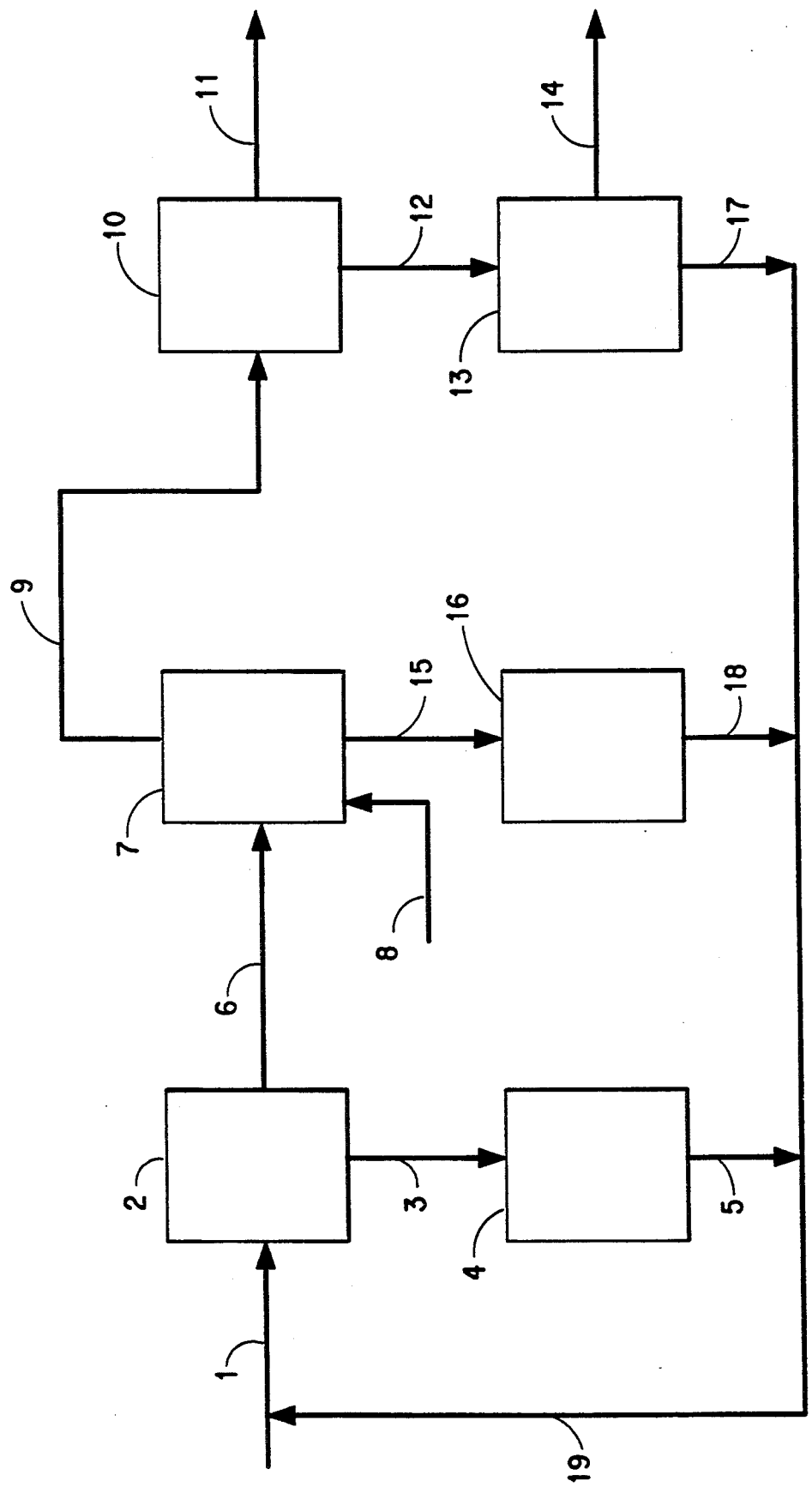

HIGH YIELD RECYCLE PROCESS FOR LACTIDE

This application is a continuation of application Ser. No. 552,217, filed Jul. 13, 1990, now abandoned.

FIELD OF THE INVENTION

This invention relates to processes for recovering recyclable lactic acid values from (A) crude lactide containing such acid values as impurities and (B) polylactic acid residues produced in the depolymerization of polylactic acid to lactide.

It also relates to a multiple solvent use process for removing recyclable water-soluble lactic acid values from impure lactide containing same and for recovering the lactide as high purity polymer grade material.

It further relates to a hydrolytic process for converting polylactic acid residues to recyclable lactic acid values.

The invention still further relates to a high yield lactide process wherein the lactic acid values removed from crude lactide and recovered from residual polylactic acid are recycled for the production of additional quantities of lactide.

BACKGROUND OF THE INVENTION

Lactide is polymerizable to high molecular weight polylactic acids which are of great interest for their hydrolytic and biodegradable properties. For example, they have long been of interest for such biomedical uses as sutures and staples. More recently, they have become of interest for the manufacture of articles of commerce for non-biomedical uses that would be degradable in the environment, in particular hydrolytically, to environmentally acceptable products. For most, if not all such uses, it is preferred the degradable polymer be made from L-lactide However, lactide made by existing technology is too costly for such non-medical uses because of low yields and by-product information.

Lactide is most conveniently prepared by polymerizing lactic acid to a relatively low molecular weight (oligomeric) polylactic acid, then heating the oligomer, generally in the presence of a catalyst, as is well known in the art, to depolymerize it to lactide which is recovered as a component of a vapor product stream. A discussion of conventional methods for producing lactide can be found in the following documents: Gruter et al., U.S. Pat. No. 1,095,205 (1914); Lowe, U.S. Pat. No. 2,668,162 (1954); Bhatia, U.S. Pat. No. 4,835,293 (1989); Bellis U.S. Pat. No. 4,727,163 (1988); Muller, Ger. Patent Application Publication Numbers 3632103 and 3708915 (1988).

Such processes suffer in that they require rather long reaction times at high temperatures for the depolymerization reaction, and generate several waste streams. The lactide product stream contains by-product lactic acid and low molecular weight polylactic acid which constitute a yield loss. Since the polymer-to-lactide yields are generally low, it is desirable to be able to recover the lactic and polylactic acids from the product stream and recycle them for the production of additional lactide.

Further, the rather long residence times at the high temperatures employed often results in side reactions leading, for example, to unwanted isomers, including meso lactide, charring of the polymer and consequently difficult to handle reactor heels.

The reactor heels also constitute a yield loss inasmuch as continued heating under depolymerization conditions generally fails to generate sufficient additional lactide to make such operation economically feasible. Further, it results in increased formation of the unwanted meso-isomer and other by-products which further complicate the downstream recovery operation.

Bhatia U.S. Pat. No. 4,835,293 discloses a gas-assisted depolymerization process for the production of dimeric cyclic esters such as lactide wherein a stream of an inert gas is employed to strip the cyclic ester from the reaction zone along with any volatile hydroxycarboxylic acid also formed therein. The resulting gaseous product stream is scrubbed with a polar organic solvent to recover the cyclic ester. The solvents include alcohols, ethers, esters and ketones, with use of isopropyl alcohol exemplifying the recovery of glycolide from its impurities. Isopropyl alcohol as scrubbing solvent solubilizes the hydroxycarboxylic acids and any water of reaction, thereby enabling the recovery of glycolide directly from the scrubbing medium as a substantially insoluble filterable crystalline solid.

Use of an alcohol, however, as the scrubbing solvent for the recovery of L-lactide from a vapor product stream is not entirely satisfactory. It reacts in the alcoholic solution to form alkyl lactate, which not only constitutes a yield loss but further increases the solubility of lactide in the scrubbing solution, further aggravating the yield loss problem. Also, since the starting L-lactic acid used to make lactide always contains some D-lactic acid, the reaction product always contains some meso-isomer. Meso-lactide is more soluble in alcohol than L-lactide and tends to increase the solubility of the L-isomer. Thus, when the lactic acid values are recovered from the alcoholic filtrate they are accompanied by the meso lactide, which continues to build up in the system and eventually results in greater solubility losses of L-lactide and decreased efficiency of the process.

On the other hand, use of a non-hydroxylic scrubbing solvent such as acetone, for example, which is non-reactive towards lactide and in which lactide is highly soluble, likewise presents difficulties inasmuch as such polar solvent solubilizes the by-product hydroxycarboxylic acids as well, so that further processing would be required to separate the lactide from the acids.

Water as a scrubbing solvent is also unsatisfactory in that heat transfer to it is much faster then mass transfer; consequently, lactide precipitates as fog of particles, difficult to capture in the absence of specialized and costly equipment.

Thus, a need exists for a means that provides for the substantially complete recovery of lactide from a vapor stream that also contains lactic acid and open-chain dimer, and at the same time provides for the substantially complete recovery of the acid values for recycle, in a way that avoids the build-up of the meso-isomer in the system. Also, there is a need for a process for the recovery of potential lactic acid values in polylactic acid residues that have little or no value as lactide sources in the depolymerization reaction.

It is an object of this invention to provide processes that meet the above needs. It is another object to provide an integrated high yield lactide process wherein the lactic acid values removed from the crude lactide vapor stream and recovered from the residual polylactic acid are recycled for the production of additional quantities of lactide.

BRIEF DESCRIPTION OF THE DRAWING

FIG. 1 is a schematic drawing of an apparatus which may be used to practice the invention.

SUMMARY OF THE INVENTION

A process for separating lactide from impure lactide containing minor amounts of lactic acid and/or a water-soluble polylactic acid, which process comprises
  (i) contacting the impure lactide with (A) a non-reactive organic solvent for lactide and (B) water in amounts sufficient to form a mixture capable of forming two phases when settled;
  (ii) allowing the mixture to settle and form two phases, one phase comprising lactide substantially free of lactic acid and said other water-soluble impurities and the other phase comprising an aqueous solution of the carboxylic acid impurities substantially free of lactide, and
  (iii) separating the lactide phase from the aqueous phase.

Other specific and independent embodiments include: recovering the lactic acid values, that is, lactic acid and the water-soluble oligomers thereof, from the aqueous phase; recycling the lactic acid values to a process for the production of polylactic acid, preferably polylactic acid for the production of lactide by depolymerization thereof; employing a solvent as defined that is water-miscible, such as acetone, so that the lactide phase formed upon dilution comprises a precipitate of lactide and the aqueous phase contains the water-soluble impurities of the impure lactide and the water-miscible solvent; employing a solvent that is water-immiscible, such as methyl isobutyl ketone, so that the lactide phase comprises a solution of the lactide in said solvent and the aqueous phase comprises the lactic acid values, as described above; employing as the impure lactide a gas product stream comprising an inert carrier gas and said impure lactide, including such gas product stream produced on depolymerizing polylactic acid in the presence of a stream of carrier gas, more particularly as produced by the gas-assisted depolymerization process for the production of dimeric cyclic esters described in Bhatia U.S. Pat. No. 4,835,293; subjecting polylactic acid residues from the depolymerization step in the production of lactide, including from the depolymerization step of the gas-assisted process referenced above, to controlled hydrolysis, whereby to convert such depolymerization residue to aqueous lactic acid optionally containing water-soluble polylactic acid; integrating the lactide-recovering and the lactic acid values-recovering embodiments so as to recover lactide substantially completely and substantially free of its impurities, to recover and recycle the lactic acid values from the impure lactide substantially completely, and to recover and recycle the lactic acid values substantially completely from a polylactic acid depolymerization residue, said integrated process, through recycle of the recovered lactic acid values from the impure lactide and the depolymerization residues, constituting a high yield lactide process.

It will be understood that the term lactide as used herein is meant to include L-lactide, D-lactide, mixtures of D- and L-lactide containing a preponderance of L- or D-lactide, and mesolactide.

Also the term lactic acid values is meant to include water-soluble low molecular weight polylactic acids, in addition to monomeric lactic acid itself, and mixtures thereof.

DETAILED DESCRIPTION OF THE INVENTION

The invention process is applicable to the treatment of impure lactide compositions containing water-soluble lactic acid and polylactic acid, whatever the source and physical state of the impure lactide. It is particularly applicable to the treatment of a vapor stream containing the impure lactide composition which comprises solvent scrubbing of the vapor stream. It is more particularly applicable to the recovery of lactide and its lactic acid values from a vapor stream comprising an inert carrier gas and said impure lactide by solvent scrubbing as described in Bhatia U.S. Pat. No. 4,835,293, but wherein the scrubbing solvent and the subsequent handling of the resulting solution is as more fully described herein.

In general the process for separating water-insoluble lactide, including the meso-isomer, from water-soluble lactic acid and oligomeric lactic acid involves contacting the impure lactide composition with (a) a non-reactive solvent for lactide and (b) water, said solvent and water being employed in amounts sufficient to form two phases, one of which is a lactide phase that is substantially free of the water-soluble impurities and the other of which is an aqueous phase that is substantially free of lactide and contains substantially all the water-soluble impurities. The organic solvent may be employed alone or as a mixture with water as the scrubbing medium.

It is preferred to first treat the impure lactide with the organic solvent to form a solution containing all the lactide and all the acid impurities, then to extract the acid impurities with water. Alternatively, the solvent may first be evaporated and the residual lactide-lactic acid composition extracted with water to recover the acid values.

Where the impure lactide is a component of a gas product stream, the step of treating the product stream, so as to form a solution of the lactide in the organic solvent, is conveniently conducted as described in Bhatia, U.S. Pat. No. 4,835,293, which disclosure is incorporated herein by reference.

In one aspect of the invention, the non-reactive organic solvent will also be water-soluble, preferably miscible therewith, for example, acetone, so that the resulting two-phase system consists essentially of a precipitate of lactide and an aqueous solution containing substantially all the water-soluble lactic acid values, any water that the original impure lactide composition may have contained and substantially all the water-soluble/-miscible organic solvent. Any organic solvent, water or acids the lactide may still contain are readily removable by standard crystallization and drying techniques.

In another aspect of the invention the organic solvent is substantially insoluble in or immiscible with water so that the resulting two-phase system obtained by scrubbing the impure lactide with such solvent and subjecting the resulting solution to liquid-liquid extraction, will consist of an organic solvent phase containing the lactide and an aqueous phase containing the lactic acid values and any water that may have been present in the impure lactide composition. The lactide and the lactic acid values may be recovered from their respective solvent phases by any means known to the art, and further purified by known means, if desired.

The organic solvent may vary widely, provided it is non-reactive towards lactide under the process conditions employed for effecting the desired separation of lactide from its impurities. By non-reactive is meant that the solvent is essentially free of functional groups that react with lactide to form ring-opened products or derivatives thereof. Preferably, the organic solvent will be normally liquid compounds composed of C, H and O boiling at least about 50° C. and exhibiting a significant degree of solvency for lactide, lactic acid and the water-soluble oligomeric hydroxycarboxylic acids thereof. Included are such oxygenated compounds as ketones, ethers and esters containing up to about 8 carbon atoms, preferably not more than about 6 carbon atoms, for reasons of ease of evaporative removal.

Representative ketones are acetone, methyl ethyl ketone, methyl n- or iso-propyl ketone, methyl n- or iso-butyl ketone, diethyl ketone, ethyl propyl ketone, ethyl butyl ketone and dipropyl ketone. Those having at least 5, preferably at least 6 carbon atoms in the molecule, in particular methyl isobutyl ketone, are preferred for use in the water-immiscible solvent embodiment.

Representative ethers include methyl butyl ether, methyl amyl ether, ethyl propyl ether, ethyl butyl ether, dipropyl ether and the dimethyl ether of ethylene glycol. Such ethers are substantially immiscible with water and are suitable for use in the immiscible solvent embodiment.

Representative esters include such carboxylic esters as methyl acetate, methyl n- and iso-propionate, methyl butyrate, methyl valerate, ethyl acetate, ethyl propionate, ethyl butyrate and ethyl valerate. Of these carboxylates, those having at least 4 or 5 carbon atoms are largely insoluble in, or substantially immiscible with, water and may be used for the present purpose as the water-immiscible solvent embodiment of the invention.

It will be appreciated by those skilled in the art that these solvents may also be employed in the further purification of the lactide by crystallization and recrystallization if needed.

The invention may be better understood with reference to FIG. 1, which schematically depicts various embodiments of the invention involving: a lactic acid-to-polylactic acid converter; means for recycling unconverted lactic acid to the converter; a depolymerizer unit for depolymerizing (cracking) polylactic acid to lactide (accompanied by lactic acid value impurities) as a vapor product stream; a solvent scrubbing system for removing lactide and its impurities from the vapor product stream and for separating and recovering lactide from the impurities; means for recovering and recycling the impurities to the lactic acid-to-polylactic acid converter; means for hydrolyzing spent polylactic acid from the depolymerizer unit and recycling the thus produced lactic acid values to the lactic acid-to-polylactic acid converter.

In a typical operation, concentrated aqueous lactic acid, preferably containing about 80–90% by weight lactic acid, e.g., 88% acid as is available commercially, is fed through line 1 to converter 2 where it is further concentrated by distillation and polymerized to polylactic acid (PLA) with further removal of water-of-reaction by heating gradually to about 160°, then to 175° C. preferably under reduced pressure or with a N₂ sweep. The aqueous distillate removed during this concentration and polymerization stage is passed through 3 to concentrator 4, where it is dehydrated to concentrated lactic acid for recycle. Polylactic acid produced in 2 is sent through 6 to depolymerizer 7, where it is depolymerized at about 185°–235° C., preferably 195°–220° C., with a flow of an inert gas such as N₂ from line 8 being passed through it in an amount and at a rate sufficient to sweep out the reaction products. The gaseous product stream containing lactide, minor proportions of lactic acid and still minor proportions of volatilized water-soluble oligomers generally having 2 to 3 lactic acid units, exits the depolymerizer through 9 and enters solvent scrubber 10, where it is scrubbed with a solvent as defined, for example acetone, to form a solution of lactide and its lactic acid value impurities.

With a water-miscible solvent such as acetone, the solution is concentrated to start precipitation of lactide, and diluted with water, preferably water cooled to 0°–5° C., in an amount sufficient to precipitate the lactide substantially completely, leaving the lactic acid values in the aqueous acetone solution. Lactide, substantially free of its impurities, is separated, as by filtration or centrifugation, removed through line 11 and purified further if desired, by washing, drying and recrystallization from non-reactive solvents, e.g., toluene. When a water-immiscible solvent is employed, e.g., methyl isobutyl ketone, the organic solution produced in 10, is thoroughly extracted with water in an amount sufficient to remove substantially all the lactic acid values from the solution, and the resulting aqueous phase separated from the organic. The lactide-containing organic phase is removed via line 11 and lactide recovered from the solution by any means known to the art, e.g., solvent evaporation, crystallization and recrystallization, as necessary or desired.

The aqueous solution containing substantially all the lactic acid values and residual organic solvent is sent through line 12 to concentrator 13 where any organic solvent present is stripped therefrom, and the aqueous solution concentrated for recycle, e.g., to 88% lactic acid, the organic solvent and excess water being removed via line 14, the recycle stream through 17. The polylactic acid residue remaining in depolymerizer 7 is removed through 15 to hydrolyzer 16 and is heated with water at the boil until the residue is converted substantially completely to an aqueous solution.

The hydrolysate is filtered and concentrated, if necessary, to, for example, 88% lactic acid for recycle. Preferably, the proportion of water employed for hydrolysis will be sufficient to provide an hydrolysate having the desired lactic acid concentration. Also, one could use dilute aqueous lactic acid for hydrolysis. Lactic acid hydrolyzate for recycle leaves hydrolyzer 16 through 18, is combined with the lactic acid recycle stream 17 (from 13) and 5 (from 4) to form combined stream 19, which is recycled to line 1, then to converter 2 along with make up concentrated lactic acid.

The overall operation, representing a single illustrative recycle stage, can be repeated to achieve a lined-out recycle process wherein the amount of recycle material will equal the amount of lactic acid material generated in each pass. Recycle of recovered lactic acid enables the quantity of fresh lactic acid feed to the converter to be reduced and the overall yield of lactide thereby increased.

The steps of polymerizing lactic acid to polylactic acid and of depolymerizing polylactic acid to lactide are ordinarily and preferably conducted in the presence of a catalyst, which may be carried in the lactic acid feed stream or incorporated directly into the reaction mass. The catalyst can be any of those known in the art for promoting condensation of the alpha-hydroxycarboxylic component to oligomers and for promoting cyclic ester formation. The catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn(II) carboxylates, especially those that are soluble in the feed stream and the resulting reaction mixture, exemplified by Sn bis (2-ethylhexanoate), commonly referred to as stannous octoate.

The catalyst is employed in catalytically effective amounts, which can vary widely depending upon reaction conditions. The optimum catalytically effective amounts for any particular system can readily be determined through trial runs. For example, with a Sn (II) octoate the quantity is generally such that the reaction mass contains from about 0.1 to 1.5% by weight, preferably from about 0.3 to 0.7% by weight.

It will be noted hydrolyzed residue (stream 18) will normally contain the catalytic metal, which is also recycled to the converter making unnecessary the addition of fresh catalyst except for small make-up quantities to compensate for process losses.

The gaseous agent for entraining/carrying/sweeping the lactide and the impurities out of the reaction mixture and out of the depolymerization reactor 7 may be any substance that is gaseous, stable and non-reactive at the operating temperatures and pressures and is inert to the starting material, reaction mass components and reaction products. It may be normally gaseous, such as nitrogen, argon, carbon monoxide or dioxide or low molecular weight hydrocarbon. it may be normally non-gaseous but gaseous at reaction temperature and pressure. Preferred is nitrogen for its inertness and ready availability. Preferably the inert gas will be preheated to the operating temperature and will be injected below the surface of the reaction mass in the reaction zone; for example, below the agitator of a stirred tank reactor or at the bottom of a vertically disposed reactor.

The flow rate of the gas should be sufficiently high so as not to limit the lactide stripping rate. If the flow rate is too low, the conversion to lactide may be adversely affected and its production rate limited since the gas functions importantly to carry it as vapor out of the reactor.

An inert gas flow may also be advantageously used to sweep gross water and water-of-reaction from lactic acid during its concentration and polymerization to polylylactic acid in converter 2.

The depolymerizer reactor design is not critical provided it has means for introducing a polylactic acid feed stream, means for introducing a gaseous lactide-stripping agent into the reaction zone such that it directly and intimately contacts the polylactic composition so as to give high gas-liquid interfacial contact and has means for removing a gaseous stream containing cyclic ester. Thus the reactor may be a stirred tank equipped with gas-sparging means, preferably one which admits the gas directly under the agitator. The reactor may also be a packed or sieve-plate column, or it may be of any other design known in the art for effecting intimate gas-liquid contact.

Further, lactic acid-to-polylactic acid converter 2 may be combined with depolymerizer 7 into a single reaction zone that (a) permits the formation of an in situ produced polylactic acid and its subsequent depolymerization to lactide, (b) has means for introducing the gaseous stripping agent, and (c) has means for removing the gaseous product stream containing lactide and its lactic acid impurities from the reaction zone.

The pressure throughout the reactor system may vary from sub-atmospheric to atmospheric and super-atmospheric. Preferably it is about atmospheric, plus a small back pressure exerted on the gas product stream by the downstream equipment, which should be designed to keep the back pressure as low as practical, for example, to keep the back pressure as low as 5 psig.

Likewise the product stream recovery and processing system may be any of those known to the art. One such reactor and product recovery system is disclosed in Bhatia U.S. Pat. No. 4,835,293 which disclosure is incorporated herein by reference.

EXAMPLE

This example illustrates the high yield multi-stage recycle embodiment of the invention conducted in accordance with the sequence depicted in FIG. 1 and outlined above.

A. An oligomer of L-lactic acid was prepared by gradually heating a mixture of 378 grams of 88% aqueous L-lactic acid (equivalent to 266 grams of lactide) and 1.26 grams of stannous octoate, over a 2-hour period to 164° C., while removing free water and water of condensation in a small stream of $N_2$ gas. 98.6 gms. of aqueous distillate was collected during this period. The reaction mass was held at 164°–188° C. for another 0.25 hour, and the rate of removal of distillate slowed to essentially nil. The aqueous distillate from this operation, which contained lactic acid volatilized during the stripping and condensing of the feed material, was concentrated under reduced pressure to 23.8 gms of conc. lactic acid (approximately 100 to 110%), which was reserved for recycling.

B. The reaction mass from A was gradually heated under agitation to 214° C., while a stream of $N_2$ was passed through at the rate of 0.45 scfm, over a 1-hour period. The stream of $N_2$ gas exiting the reactor contained lactide and minor amounts of lactic acid and water. Upon completion of the depolymerization stage, 70 gms of polymeric residue remained. To 54.8 gms of this material was added 23.5 gms of water and the mixture was heated under reflux for 45 minutes to yield 78.3 gms of crude 88% lactic acid, which was reserved for recycling.

C. The lactide product and its lactic acid impurity were recovered from the $N_2$ gas stream by scrubbing with acetone. The acetone solution was partially evaporated to a point where lactide began to crystallize out; chilled water was added to precipitate the rest of the lactide. Filtration and drying by passing through the filter cake a stream of dry $N_2$ gas and then drying at room temperature under reduced pressure gave 132 gms (50% yield) of good quality white, crystalline lactide. The aqueous acetone filtrate containing the lactic acid values was stripped of acetone under reduced pressure and further concentrated to 26.8 gms of conc. lactic acid, which was reserved for recycling.

D. The aqueous lactic solutions from A, B and C, reserved for recycling and containing lactic acid values equivalent to 110.8 gms of lactide, were combined with 240 gms of fresh 88% lactic acid equivalent to 169 gms of lactide, and the reaction sequence described under A, B and C was repeated twice more. The details of these runs and the results obtained are tabulated below.

| Feed, Gms. Fresh Lactide | | | Recovered LA Values, Gms. | | | Recovered Lactide | |
|---|---|---|---|---|---|---|---|
| Run | LA | Equiv. | A | B | C | Gms. | % Yield[a] |
| 1 | 378 | 266 | 23.8 | 78.3 | 26.8 | 132 | 50 |
| 2 | 240 | 169 | 17.0 | 113 | 24.0 | 118 | 70 |
| 3 | 207 | 146 | 16.2 | 117 | 31.0 | 122 | 84 |

[a]Based on fresh LA (lactic acid) feed.

I claim:

1. A process for recovering recyclable lactic acid from impure lactide comprising:
   (i) contacting the impure lactide with (A) a non-reactive solvent for lactide and, (B) water in amounts sufficient to form a mixture capable of forming two phases;
   (ii) allowing the mixture to settle and form two phases, a first phase comprising lactide substantially free of lactic acid and a second phase comprising an aqueous solution of lactic acid substantially free of lactide;
   (iii) separating the first phase from the second phase; and
   (iv) recovering recyclable lactic acid from the second phase.

2. The process of claim 1 wherein the lactic acid from the second phase is recycled to a process for converting said lactic acid to lactide.

3. The process of claim 1 wherein the solvent comprises a water-miscible solvent and the resulting two phases comprise, a first phase comprising a precipitate of lactide and a second phase comprising an aqueous solution of the solvent, lactic acid and any water that my have been present in the impure lactide.

4. The process of claim 1 wherein the impure lactide is contacted with a solvent comprising an organic solvent, in an amount sufficient to solubilize the lactide and impurities thereof and the resulting solution is diluted with water in an amount sufficient to precipitate the lactide.

5. The process of claim 1 wherein the solvent comprises a water-immiscible solvent and the resulting two phases comprise, a first phase comprising a water-immiscible solution of the lactide in said solvent and a second phase comprising a separate aqueous solution of the lactic acid and any water that may have been present in the impure lactide.

6. The process of claim 1 wherein the impure lactide comprises a component of a gas stream comprising an inert carrier gas.

7. A process for recovering recyclable lactic acid values from a water-insoluble polylactic acid residue comprising:
   (i) heating the residue in the presence of a sufficient quantity of water at a temperature, pressure and time sufficient to hydrolyze at least a substantial proportion of the residue to form an aqueous solution comprising at least one of lactic acid and a water-soluble polylactic acid; and
   (ii) separating the aqueous solution from any remaining residue.

8. The process of claim 7 wherein the quantity of water is sufficient to result in an aqueous solution comprising at least about 50% by weight of said lactic acids.

9. The process of claim 7 wherein the aqueous solution is recycled to a process for converting lactic acid to lactide.

10. A process for making lactide comprising:
    (a) converting lactic acid to a depolymerizable polylactic acid;
    (b) passing an inert gas through said depolymerizable polylactide;
    (c) depolymerizing said polylactic acid at a suitable temperature and pressure, while in the presence of said inert gas to form a gas product stream comprising lactide and lactic acid;
    (d) scrubbing the gas product stream with a solvent which removes at least a portion of the lactide and lactic acid from the gas stream; wherein the scrubbing solvent comprises a solvent that is non-reactive towards lactide and lactic acid and solubilizes lactide and lactic acid;
    (e) employing the solvent in an amount sufficient to form a solution of said lactide and lactic acid;
    (f) contacting the solution formed in step (e) with a sufficient amount of water to form two phases, the first phase comprising lactide substantially free of lactic acid and the second phase comprising an aqueous solution that is substantially free of lactide and contains substantially all of the lactic acid;
    (g) separating the two phases;
    (h) recovering lactide from the first phase, and;
    (i) recovering recyclable lactic acid from the second phase and recycling it to step (a) for the production of polylactic acid and lactide.

11. The process of claim 10 wherein depolymerization step (c) produces a water-insoluble polylactic acid residue and the process further comprises hydrolyzing the residue to form an aqueous lactic acid solution and recycling the lactic acid solution to step (a) for the production of polylactic acid and lactide.

12. The process of claim 10 wherein the scrubbing solvent comprises a solvent which is miscible with water and the resulting solution, which contains lactide and lactic acid, is concentrated to near saturation and is then diluted with water in an amount sufficient to substantially completely precipitate the lactide.

13. The process of claim 12 wherein the solvent is acetone and the resulting aqueous phase contains substantially all the acetone as well as substantially all the lactic acid.

14. The process of claim 10 wherein the scrubbing solvent comprises a water-immiscible solvent and the resulting solution, which contains the lactide and lactic acid, is extracted with water to form a liquid organic phase comprising substantially all the lactide and a phase comprising substantially all the lactic acid.

15. The process of claim 14 wherein the water immiscible solvent is methyl isobutyl ketone.

* * * * *

UNITED STATES PATENT AND TRADEMARK OFFICE
CERTIFICATE OF CORRECTION

PATENT NO. : 5,136,057
DATED : August 4, 1992
INVENTOR(S) : Kamleh K. Bhatia

It is certified that error appears in the above-indentified patent and that said Letters Patent is hereby corrected as shown below:

On the title page: Item [75] Inventors: add -- Melville E. D. Hillman, James D. Browning and Herman P. Benecke as named inventors.

Signed and Sealed this

Ninth Day of January, 1996

Attest:

BRUCE LEHMAN

Attesting Officer

Commissioner of Patents and Trademarks